(12) United States Patent
Yan

(10) Patent No.: US 12,102,743 B2
(45) Date of Patent: Oct. 1, 2024

(54) BIOREACTOR AND BIOLOGICAL REACTION SYSTEM

(71) Applicants: SHANGHAI CELLIVER BIOTECHNOLOGY CO., LTD., Shanghai (CN); SHANGHAI CRYOWISE MEDICAL TECHNOLOGY CO., LTD., Shanghai (CN)

(72) Inventor: Hexin Yan, Shanghai (CN)

(73) Assignees: SHANGHAI CELLIVER BIOTECHNOLOGY CO., LTD., Shanghai (CN); SHANGHAI CRYOWISE MEDICAL TECHNOLOGY CO., LTD., Shanghai (CN)

( * ) Notice: Subject to any disclaimer, the term of this patent is extended or adjusted under 35 U.S.C. 154(b) by 548 days.

(21) Appl. No.: 17/614,328

(22) PCT Filed: Aug. 7, 2019

(86) PCT No.: PCT/CN2019/099681
§ 371 (c)(1),
(2) Date: Nov. 24, 2021

(87) PCT Pub. No.: WO2020/237832
PCT Pub. Date: Mar. 12, 2020

(65) Prior Publication Data
US 2022/0218887 A1    Jul. 14, 2022

(30) Foreign Application Priority Data
May 24, 2019    (CN) .......................... 201910436368.5

(51) Int. Cl.
*A61M 1/16*    (2006.01)
*A61M 1/34*    (2006.01)
*A61M 1/36*    (2006.01)

(52) U.S. Cl.
CPC ......... *A61M 1/1621* (2014.02); *A61M 1/3489* (2014.02); *A61M 1/3689* (2014.02);
(Continued)

(58) Field of Classification Search
CPC .............. A61M 1/1621; A61M 1/3489; A61M 1/3689; A61M 2205/3334; A61M 2205/7518
See application file for complete search history.

(56) References Cited

U.S. PATENT DOCUMENTS

2008/0311650 A1    12/2008    Jakob et al.
2015/0064780 A1*   3/2015    Hopkins ................ C12M 29/10
                                                               435/325

FOREIGN PATENT DOCUMENTS

CN    101129276 A    2/2008
CN    103946365 A    7/2014
(Continued)

OTHER PUBLICATIONS

International Search Report of PCT Patent Application No. PCT/CN2019/099681 issued on Feb. 12, 2020.

*Primary Examiner* — Bradley R Spies
*Assistant Examiner* — Jeannie Mcdermott

(57) ABSTRACT

A bioreactor has a cover, a container body, a sealing portion, a driving portion and a liquid guide portion. A ventilation structure and a bacteria-retaining sealing breathable structure provided in the cover, a cleaning liquid inlet portion penetrates the bottom of the driving portion, and a liquid inlet portion and a liquid outlet portion of the liquid guide portion are arranged penetrating a sidewall of the container body. The driving portion drives, by means of elastic defor- (Continued)

mation, a liquid to be replaced or a cleaning liquid to move up and down, such that the liquid to be replaced can enter the container body only through a gas-liquid channel, so as to subsequently prevent damage to hepatic cells due to a carrier bearing a shearing force, and enable the liquid to be replaced to gain full contact with the carrier. Further provided is a bioreaction system.

16 Claims, 6 Drawing Sheets

(52) U.S. Cl.
CPC ............... *A61M 2205/3334* (2013.01); *A61M 2205/7518* (2013.01)

(56) References Cited

FOREIGN PATENT DOCUMENTS

| | | |
|---|---|---|
| CN | 205256967 U | 5/2016 |
| CN | 106620916 A | 5/2017 |
| CN | 207445274 U | 6/2018 |
| WO | 2005108550 A1 | 11/2005 |
| WO | 2013152036 A1 | 10/2013 |

* cited by examiner

111

BIOREACTOR AND BIOLOGICAL REACTION SYSTEM

CROSS-REFERENCE TO RELATED APPLICATION

This application is a National Phase Application of PCT Application No. PCT/CN2019/099681 filed on Aug. 7, 2019, which claims the priority benefit of China application serial no. CN201910436368.5, filed May 24, 2019, the full disclosure of which is incorporated herein by reference.

BACKGROUND

1. Field

The present invention relates to the technical field of medical equipment, in particular to a bioreactor and a biological reaction system.

2. Description of the Related Art

Liver failure is the end-stage manifestation of various liver diseases. The lack of donors and the high technical difficulty have greatly restricted the extensive development of liver transplantation. The bioartificial liver uses a bioreactor outside of the body to use human or animal-derived hepatic cells to replace the liver that cannot perform biological functions in the body to perform its compensatory function, providing an effective means for the treatment of liver failure.

The bioreactor is the core part of the bioartificial liver. It serves as a place where the patient's blood or plasma interacts with hepatic cells and exchanges substances. Its performance is directly related to the efficiency and effectiveness of artificial liver support. The ideal bioreactor is a dynamic system. With the optimization of the control system of the bioreactor itself, it should be able to better control the mass transfer inside the reactor. On the one hand, the hepatic cells can fully perform in the patient's plasma or culture fluid. Accordingly, substance exchange can more effectively detoxify the plasma or absorb nutrients in the culture fluid. On the other hand, sufficient and effective oxygen supply and exchange are beneficial to maintain the activity and function of hepatic cells.

The Chinese invention patent application with publication number CN106620916A discloses an artificial liver reactor, which introduces plasma or cell culture fluid to be replaced into a cell culture flask through a peristaltic pump, and drives the liquid surface to move up and down to make the fluid to be replaced or cells culture fluid exchanges substances with the carrier in the cell culture flask. At the same time, the carrier can exchange substances with the air. However, the artificial liver reactor disclosed in CN106620916A is provided with multiple input pipes and output pipes, and correspondingly provided with multiple flow control valves so that the system structure is complicated. In addition, the plasma to be replaced or cell culture fluid is delivered by pumping so that they are in contact with the carrier directly. Meanwhile, a higher rate will easily cause the carrier to withstand the shearing force, so the hepatic cells structure is destroyed. When the rate is too small, on the one hand, it is disadvantageous to improving work efficiency. On the other hand, it is disadvantageous to the effect of material exchange, owing to affecting full contact of the liquid to be replaced or cell culture fluid and carrier.

Therefore, it is necessary to develop a new type of biological reaction device to avoid the above-mentioned problems in the prior art.

SUMMARY

The purpose of the present invention is to provide a bioreactor applied to a bioartificial liver treatment system and a biological reaction system having the bioreactor, so as to simplify the structure and help ensure that the carrier and liquid can carry out sufficient material exchange in the treatment application, avoid the carrier to bear the effect of shearing force, and improve the safety of use at the same time.

In order to achieve the above purpose, a bioreactor of the present invention includes a cover, a container body, a sealing portion, a driving portion and a liquid guide portion. The liquid guide portion has at least a liquid inflow portion, a cleaning liquid inlet portion and a liquid outflow portion. The cover is detachably and fixedly connected to the container body, the cover is provided with a ventilation structure and a bacteria-retaining sealing breathable structure for making the internal and external air pressures of the bioreactor consistent; the liquid inflow portion has a liquid inflow pipe, and the liquid inflow pipe penetrates the sidewall of the container body to deliver the liquid to be replaced into the container body; the cleaning liquid inlet portion includes a cleaning liquid pipe and the leaning liquid pipe penetrates the bottom of the driving portion to communicate with the inside of the driving portion to deliver cleaning liquid into the driving portion; The liquid outlet portion penetrates the sidewall and bottom of the container body to discharge the replacement liquid or the cleaned liquid out of the bioreactor; the bottom of the container body is provided with a gas-liquid channel; the driving portion is used to drive the replacement liquid or the cleaning liquid to move up and down through the elastic deformation; the sealing portion is arranged along the outer sidewall of the bioreactor, and is used to connect and fix the container body and the driving portion to avoid the liquid to flow out from the sidewall of the bioreactor.

The beneficial effect of the bioreactor of the present invention is that: in the bioreactor, the cleaning liquid inlet portion penetrates the bottom of the driving portion to communicate with the inside of the driving portion, and the liquid inlet portion and the liquid outlet portion are arranged to penetrate the sidewall of the container body, so that the cleaning liquid inlet portion and the liquid inlet portion can share the liquid outlet portion, which simplifies the structure, utilizes to clean the bioreactor to remove heterologous substances before the liquid to be replaced enters the bioreactor, and avoid adverse reactions caused by the entry of heterologous substances into the human body; the liquid inflow portion and the liquid outflow portion are arranged to penetrate the sidewall of the container body and will not affect the lifting movement of the driving portion, which is helpful to perform the continuous perfusion operation and promote the timely backflow of the replacement liquid by improving work efficiency to improve the safety of use. On the other hand, the driving portion drives the replacement liquid or the cleaning liquid to move up and down by elasticity deformation, combining with the gas-liquid channel disposed at the bottom of the container body, so that the liquid to be replaced in the driving portion can enter the container body through the gas-liquid channel, it is helpful to prevent the carrier from being subjected to shearing force and destroy hepatocytes by the subsequent rate control of the driving portion, so that the liquid to be replaced forms a turbulent flow and fully contacts the carrier, which is beneficial to improve the effect of material exchange.

Preferably, the gas-liquid channel is a plurality of arc-shaped hollow structures with the same structure, and the plurality of arc-shaped hollow structures are uniformly distributed radially around the junction between the liquid outlet portion and the bottom of the container body. The beneficial effect is that: it is beneficial to the formation of turbulent flow of the liquid to be replaced, so as to fully contact the carrier, and is beneficial to improve the effect of substance exchange.

Preferably, the driving portion is a bellow pipe structure with an open end.

Preferably, the container body and the cover are detachably and fixedly connected by threaded coupled.

Preferably, the ventilation structure is arranged on the top of the cover, the bacteria-retaining sealing breathable structure includes a bacteria-retaining breathable membrane, the bacteria-retaining breathable membrane is arranged on the lower end surface of the top of the cover, and the average pore diameter is less than 0.22 micron to allow gas to pass freely, make the internal and external air pressures of the bioreactor consistent, and block microorganisms in the air during use.

Further preferably, the bacteria-retaining sealing breathable structure further has a barrier to seal the open end of the container body so that the inside of the bioreactor will not be contaminated before use.

Further preferably, a positioning adjustment member is provided inside the cover, the positioning adjustment member is arranged between the bacteria-retaining breathable membrane and the barrier, and the rotation movement of the cover drives the positioning adjustment member toward the barrier, so as to destroy the sealing performance of the barrier, so that the internal and external air pressures of the bioreactor are consistent during use.

Further preferably, the barrier is a waterproof and breathable membrane.

Further preferably, the positioning adjustment member has a positioning cover and a blade, the blade is fixedly connected to the inner sidewall of the positioning cover, and the outer sidewall of the positioning cover is detachably fixedly connected to the inner sidewall of the cover, and at least part of the lower end surface of the blade is lower than the lower end surface of the positioning cover, so as to destroy the barrier and fix the partially detached barrier during the movement of the positioning cover toward the barrier to ensure the internal and external air pressure of the bioreactor consistent during use.

Further preferably, the cover further has a spacing member, so that the lower end surface of the blade is located above the barrier.

Further preferably, the spacing member is a tear ring, the tear ring divides the cover into an upper cover and a lower cover, and the upper cover is fixedly connected to the lower cover through the positioning cover, the top of the upper cover is provided with the air-permeable structure.

Further preferably, a venting fixing frame is provided inside the cover, and the venting fixing frame detachably fixes the bacteria-retaining breathable membrane in the cover.

Further preferably, a sealing gasket is further provided inside the cover body, and the sealing gasket is provided on the lower end surface of the venting fixing frame to strengthen the sealing performance between the cover and the container body.

Preferably, an elastic waterproof ring is arranged between the inner sidewall of the sealing portion, the outer sidewall of the container body and the outer sidewall of the driving portion.

Preferably, the inner sidewall of the sealing portion is provided with at least one threaded fastener to facilitate the fixation of the bioreactor.

The biological reaction system of the present invention includes the bioreactor, a liquid supply unit, a liquid drain unit, a power drive unit, and a control unit; the liquid supply unit is fixedly connected to the liquid inlet portion and the cleaning liquid inlet portion, in order to deliver the replacement liquid to the liquid inlet portion and deliver the cleaning liquid to the cleaning liquid inlet portion; the liquid drain unit is fixedly connected to the liquid outlet portion to remove the replaced liquid or the cleaned liquid from the bioreactor; the power drive unit is used to drive the driving portion to move up and down; the control unit is used to perform rate control and time control of the lifting movement, and to perform rate control and time control of the liquid supply unit and the liquid drain unit.

The beneficial effect of the biological reaction system of the present invention is that: since the biological reaction system is provided with the bioreactor, in the bioreactor, the cleaning liquid inlet portion penetrates the bottom of the driving portion to communicate with the inside of the driving portion, and the liquid inlet portion and the liquid outlet portion are arranged through the sidewall of the container body, so that the cleaning liquid inlet portion and the liquid inlet portion can share the liquid outlet portion, which simplifies the structure; on the other hand, the driving portion is used to drive the replacement liquid or the cleaning liquid to move up and down through elastic deformation, combining with the gas-liquid channel disposed at the bottom of the container body, so that the liquid to be replaced in the driving portion can enter the container body through the gas-liquid channel, which is beneficial to prevent the carrier from being subjected to shearing force and destroy the hepatic cells by controlling the rate of the driving portion, so that the liquid to be replaced forms a turbulent flow and fully contacts the carrier, which is beneficial to improve the effect of substance exchange.

BRIEF DESCRIPTION OF THE DRAWINGS

FIG. 7c is a schematic structural view of the positioning cover shown in FIG. 7a;

DETAILED DESCRIPTION

Figure 1:
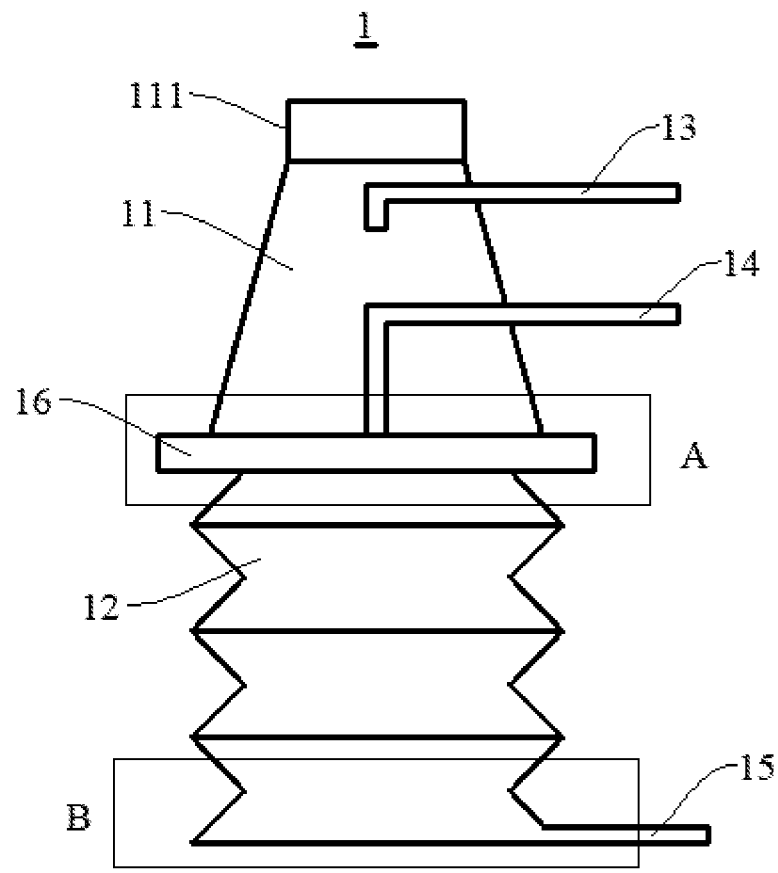
FIG. 1 is a schematic diagram of the structure of the bioreactor of the present invention.

To make the objectives, technical solutions, and advantages of the present invention clearer, the technical solutions in the embodiments of the present invention will be described clearly and completely in conjunction with the accompanying drawings of the present invention. Obviously, the described embodiments are part of the embodiments of the present invention, but not all of the embodiments. Based on the embodiments of the present invention, all other embodiments obtained by those of ordinary skill in the art without creative work shall fall within the protection scope of the present invention. Unless otherwise definition, the technical terms or scientific terms used herein shall have the usual meanings understood by those with ordinary skills in the field to which the present invention belongs. As used herein, "comprising" and other similar words mean that the elements or objects appearing before the word encompass the elements or objects listed after the word and their equivalents, without excluding other elements or objects.

Bioartificial liver treatment system is directly acting on the Human circulatory system, the working principle is to use normal hepatic cells with good activity to exchange substances in human plasma, in order to achieve adequate detoxification, and then the purified plasma formed after the detoxification treatment is mixed with isolated blood cells and returned to the human body.

A bioreactor, which is an important part of the bioartificial liver treatment system, provides a gas-liquid exchange place for the carrier supporting normal hepatic cells and the plasma separated from the blood of the patient, in order to form purified plasma.

In the actual application process, purified plasma must not be contaminated by heterologous substances before entering the human body; otherwise, it will easily cause the allergic reaction or abnormal immune response in the human body; meanwhile, it is necessary to ensure the purified plasma can be returned to the human body in time, or it may cause the patient at the risk of shock or death due to blood loss.

Aiming at the problems existing in the prior art, the embodiments of the present invention provide a bioreactor applied to a bioartificial liver treatment system. The bioreactor includes a cover, a container body, a sealing portion, a driving portion and a liquid guide portion. The liquid guide portion has at least a liquid inlet portion, a cleaning liquid inlet portion and a liquid outlet portion. The bottom of the container body is provided with a gas-liquid channel.

Specifically, the cover is detachably and fixedly connected to the container body, and the cover has a ventilation structure and a bacteria-retaining sealing breathable structure.

Specifically, the ventilation structure and the bacteria-retaining sealing breathable structure are used to make the internal and external air pressure of the bioreactor consistent. Since the ventilation structure and the bacteria-retaining sealing breathable structure allow air to enter the bioreactor, sterile air can be provided to the inside of the bioreactor, in favor of the hepatic cells maintenance or recovery the activity and function under sufficient and effective oxygen supply conditions.

The liquid inlet portion penetrates the sidewall of the container body to deliver the liquid to be replaced into the container body. The cleaning liquid inlet portion penetrates through the bottom of the driving portion to communicate with the inside of the driving portion to deliver cleaning liquid into the driving portion. The liquid outlet portion penetrates the sidewall and the bottom of the container body to discharge the replacement liquid or the cleaned liquid out of the bioreactor.

The driving portion is used for driving the replacement liquid or the cleaning liquid to move up and down through elastic deformation.

As common knowledge in the art, the normal hepatic cells for the bioartificial liver treatment are utilized on a carrier, and the carrier may be a polyethylene terephthalate fiber fabric. Nutrients such as culture medium are used in the process of loading normal hepatic cells, and the resulting slides loaded with normal hepatic cells are usually placed in a preservation solution before using to maintain cells activity. The culture medium and the preservation solution are relative heterologous substances to the human body, they may easily cause allergic reactions or abnormal immune reactions in the human body. Furthermore, the possibility of heterologous substances inside the bioreactor cannot be ruled out.

Therefore, the cleaning liquid inlet portion is arranged to penetrate the bottom of the driving portion and the liquid outlet portion penetrates the sidewall and the bottom of the container body, so that the carrier is placed after the bioreactor, and the cleaning liquid is introduced into the inside of the bioreactor through the cleaning liquid inlet portion before the liquid to be replaced enters the bioreactor, and the sidewall of the container body, the inside of the driving portion and the carried are washed by the lifting movement of the driving portion, in order to effectively remove the heterologous substances.

The sealing portion is arranged along the outer sidewall of the bioreactor and is used for fixedly connecting the container body and the driving portion.

In some embodiments of the present invention, the liquid is plasma to be replaced. The cleaning liquid is physiological saline.

In some embodiments of the present invention, the driving portion is a bellow pipe structure with an open end.

In some embodiments of the present invention, the liquid inlet portion has a liquid inlet pipe, the liquid outlet portion has a liquid outlet pipe, and the cleaning liquid inlet portion has a cleaning liquid inlet pipe.

In some embodiments of the present invention, the sealing portion has an annular waist ring and at least two threaded fasteners.

In some embodiments of the present invention, the threaded fastener has an internal thread structure, so as to be detachably fixedly connected with the operating table by means of threaded bolts.

Figure 2:
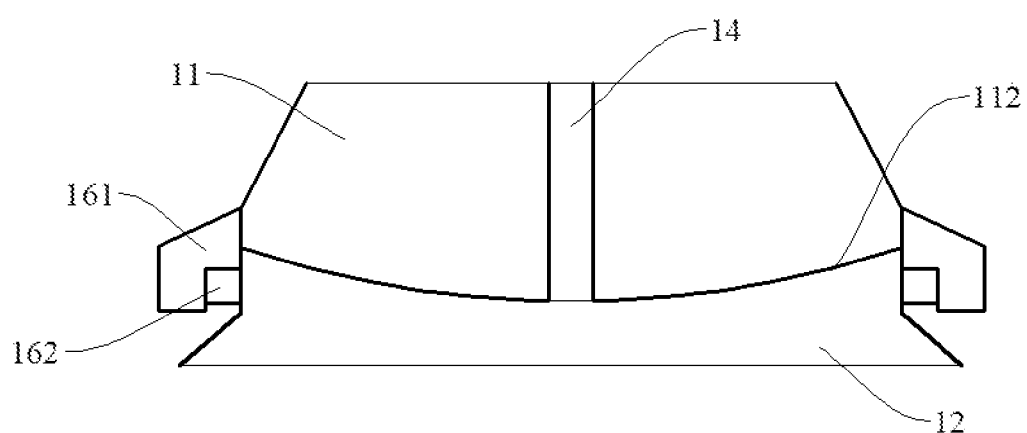
FIG. 2 is an enlarged longitudinal sectional view of part A shown in FIG. 1.

FIG. 1 is a schematic diagram of the structure of a bioreactor according to some embodiments of the invention. FIG. 2 is an enlarged longitudinal sectional view of part A shown in FIG. 1.

As shown in FIG. 1, the bioreactor 1 has a cover (not shown in the figure), a container body 11, a bellow pipe 12, a liquid inlet pipe 13, a liquid outlet pipe 14, a cleaning liquid inlet pipe 15 and a sealing portion 16. The top of the container body 11 has a columnar structure 111, and the outer sidewall is a tapered structure. The cover (not shown in the figure) is used to be arranged inside the columnar structure 111 to be detachably fixedly connected to the container body 11.

As shown in FIG. 1 and FIG. 2, the liquid inlet pipe 13 and the liquid outlet pipe 14 are both L-shaped pipes. The parallel pipes of the liquid inlet pipe 13 and the parallel pipes of the liquid outlet pipe 14 both penetrate the outer sidewall of the container body 11 and are arranged parallel to each other. The vertical pipe of the liquid outlet pipe 14 penetrates the concave arc-shaped bottom 112 of the container body 11 along the centerline of the container body 11 to communicate with the inside of the bellow pipe 12. The vertical pipe of the liquid inlet pipe 13 is located directly above the vertical pipe of the liquid inlet pipe 13.

The liquid inlet pipe 13 is arranged to penetrate the sidewall of the container body 11, the liquid outlet pipe 14 is arranged to penetrate the sidewall and the bottom of the container body 11, the cleaning liquid inlet pipe 15 penetrates the container body 11 from the liquid outlet pipe 14, and has the following beneficial effects:

On the one hand, the lifting movement of the bellow pipe 12 will not be affected, which is beneficial to ensure well material exchange.

On the other hand, it is beneficial to continuously connect the filling process of the liquid to be replaced through the liquid inlet pipe 13 and the discharge process of the cleaned liquid through the liquid outlet pipe 14, thereby ensuring the continuous operation of the overall treatment process, improving the work efficiency, and facilitating the replacement of the liquid, for example, the purified plasma is returned to the human body in time.

Furthermore, when the cleaning liquid or the liquid to be replaced in the bellow pipe 12 does not contact the carrier with hepatic cells, the bellow pipe 12 can be controlled to move up and down at a relatively large rate, and when the cleaning liquid or the liquid to be replaced is in contact with the carrier loaded with hepatic cells, the bellow pipe 12 can be used to control reasonable rate control to prevent the liver cells from being damaged due to the excessive shearing force, so as to ensure well material exchange effect.

In some embodiments of the present invention, the open end surface of the driving portion is bonded and fixed to the bottom of the container body, and then the sealing portion is used to strengthen the sealing performance between the container body and the driving portion to avoid liquid to flow out from the sidewall of the bioreactor.

The sealing portion is arranged on the outer sidewall of the bioreactor to seal the junction between the driving portion and the container body, which also increases the effective use area of the bottom of the container body. That is, more carriers loaded with hepatic cells can be placed at the bottom of the container body to participate in the material exchange with the liquid to be replaced, which also increases the amount of the liquid to be replaced that enters the container body from the driving portion, thereby benefiting the work efficiency of the bioreactor, so that the formed replacement liquid can flow back in time.

As shown in FIG. 1 and FIG. 2, the sealing portion 16 is arranged along the outer sidewall of the bioreactor 1. Specifically, the sealing portion 16 has an annular waist ring 161 and two threaded fasteners 162 with the same structure. The longitudinal section of the annular waist ring 161 is an irregular hexagon, and one end surface of the annular waist ring 161 and two threaded fasteners with the structure. The longitudinal section of the annular waist ring 161 is an irregular hexagon, the annular waist ring 161 closely adheres to a part of the outer sidewall of the lower part of the container body 11 and a part of the outer sidewall of the top of the bellow pipe 12, which enhances the sealing performance between the container body 11 and the bellow pipe 12. An annular channel structure (not shown in the figure) is formed between the inner sidewall of the annular waist ring 161 and the outer sidewall of the bellow pipe 12, and the threaded fastener 162 is arranged on the inner sidewall of the annular waist ring 161.

In some embodiments of the present invention, the outer sidewall of the annular waist ring 161 is provided with a plurality of anti-skid protrusion structures, and the height of the anti-skid protrusion structure along the diameter direction of the bellow pipe 12 is 0.5 cm.

In some embodiments of the present invention, an elastic waterproof ring is arranged between one end surface of the annular waist ring and a part of the outer sidewall of the lower part of the container body and a part of the outer sidewall of the top of the bellow pipe, and the annular waist ring passes through the elastic waterproof ring further enhances the sealing performance between the container body and the driving portion.

Figure 3A:
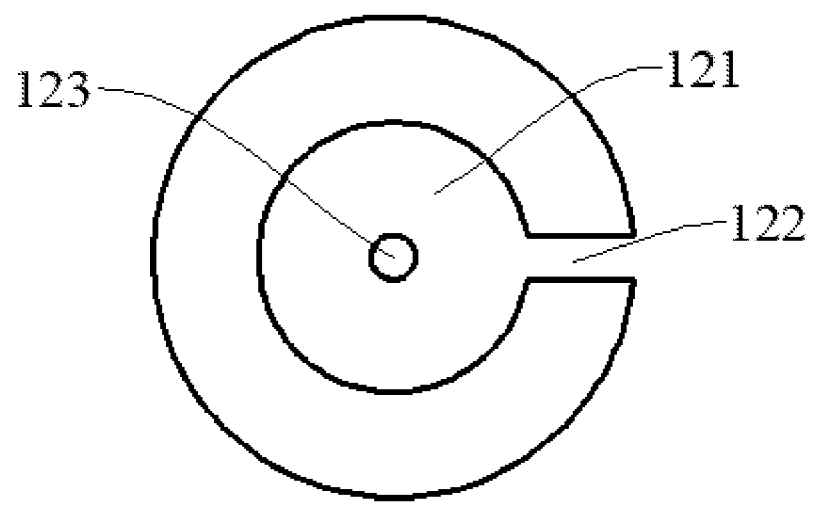
FIG. 3a is a schematic diagram of the bottom structure of the bellow pipe shown in FIG. 1.
Figure 3B:
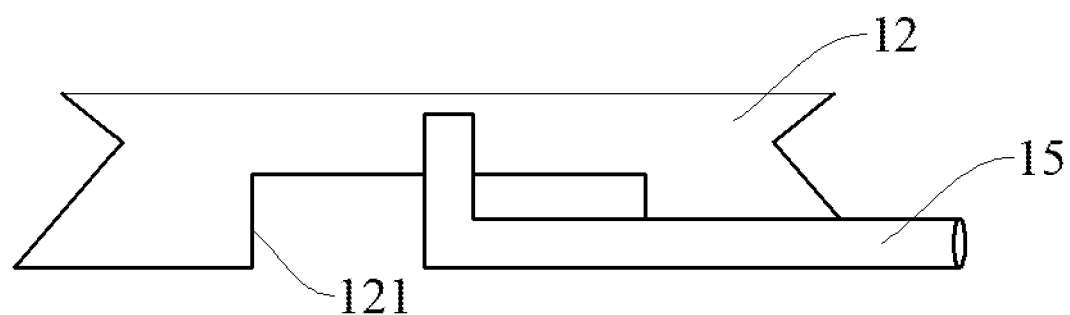
FIG. 3b is a longitudinal sectional view of part B shown in FIG. 1.

FIG. 3a is a schematic diagram of the bottom structure of the bellow pipe shown in FIG. 1. FIG. 3b is a longitudinal sectional view of part B shown in FIG. 1.

As shown in FIG. 1 and FIG. 3a, the bottom of the bellow pipe 12 has a bottom groove 121 and a bottom channel 122 communicating with the bottom groove 121, and a through hole 123 is disposed in the middle of the bottom groove 121.

As shown in FIG. 3a and FIG. 3b, the cleaning liquid inlet pipe 15 is an L-shaped pipe. The vertical pipe of the cleaning liquid inlet pipe 15 penetrates the through hole 123 to communicate with the inside of the bellow pipe 12. The parallel pipe of the cleaning liquid inlet pipe 15 is embedded in the bottom channel 122 and extends to the outside of the bellow pipe 12 to facilitate the horizontal placement of the bioreactor 1.

In some embodiments of the present invention, the bottom of the container has a concave arc-shaped bottom to facilitate placement of the carrier. The carrier is loaded with hepatic cells.

In some embodiments of the present invention, the gas-liquid channel is a plurality of arc-shaped hollow structures with the same structure, and the plurality of arc-shaped hollow structures are radially evenly distributed around the junction of the liquid outlet portion and the bottom of the container body. It is conducive to the formation of turbulence after the plasma to be replaced passes through the arc-shaped hollow structure. On the one hand, it avoids the problem of the destruction of the hepatic cells caused by the shearing force of the carrier, and on the other hand, it is beneficial to drive the carrier floats slightly, so that the plasma to be replaced and the hepatic cells undergo sufficient liquid phase material exchange.

Figure 4:
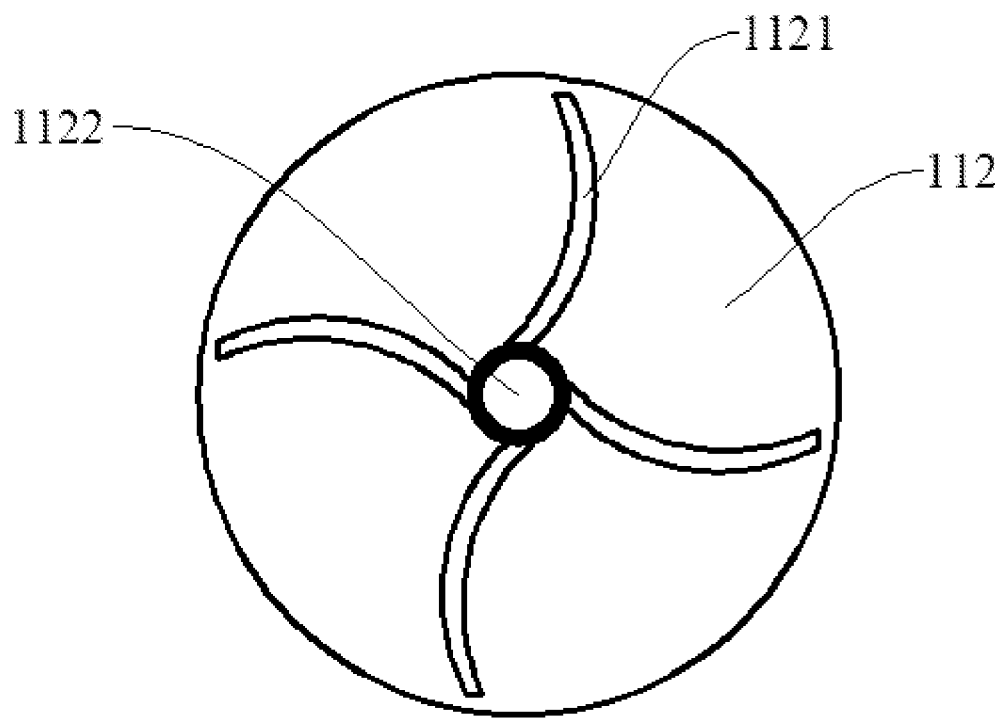
FIG. 4 is a schematic diagram of the bottom structure of the container body shown in FIG. 1.

FIG. 4 is a schematic diagram of the bottom structure of the container body shown in FIG. 1.

As shown in FIG. 2 and FIG. 4, the center of the concave arc-shaped bottom 112 is provided with an engaging through hole 1122 to be fixedly connected with the vertical pipe of the liquid outlet 14. The surface of the concave arc-shaped bottom 112 is provided with four arc-shaped hollow structures 1121 with the same structure around the joint through hole 1122, and the four arc-shaped hollow structures 1121 are evenly distributed in a radial pattern, so that the container body 11 and a gas-liquid channel is formed between the bellow pipe 12.

In some embodiments of the present invention, the open end of the container body and the cover are detachably and fixedly connected in a threaded coupled manner, and the upper end surface of the cover is not higher than the upper end surface of the container body.

In some embodiments of the present invention, the open end of the container body has a groove, and a locking structure is provided in the middle of the groove, and the locking structure is detachably fixedly connected with the lid in a threaded coupled manner.

In some specific embodiments of the present invention, the locking structure is a locking interface.

Figure 5:
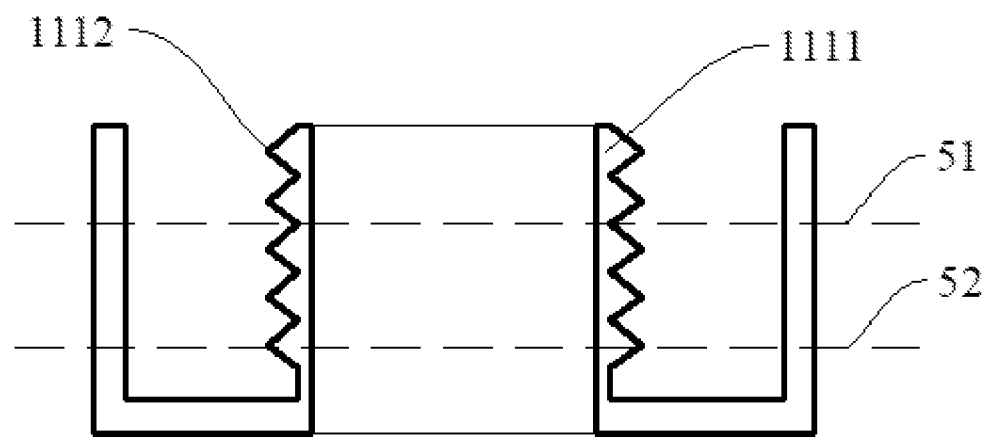
FIG. 5 is a longitudinal sectional view of the columnar structure shown in FIG. 1.

FIG. 5 is a longitudinal sectional view of the columnar structure shown in FIG. 1.

As shown in FIG. 1 and FIG. 5, the columnar structure 111 is a hollow cylinder with an end opening, and a locking interface 1111 is provided at the bottom of the columnar structure 111. The locking interface 1111 is a hollow structure with two end openings and one end penetrates the bottom of the cylindrical structure 111 to communicate with the inside of the container body 11. The outer sidewall of the locking interface 1111 has an external thread 1112, which is detachably and fixedly connected with the cover body (not shown in the figure) by threaded coupled.

In some embodiments of the present invention, the bacteria-retaining sealing breathable structure includes a bacteria-retaining breathable membrane, the top of the cover is provided with an air-permeable structure, and the bacteria-retaining breathable membrane and the bacteria-retaining sealing breathable structure make the internal and external air pressures are consistent during the using process of the bioreactor. In some embodiments of the present invention, the average pore diameter of the bacteria-retaining breathable membrane is less than 0.22 micron to allow gas to pass freely and block microorganisms in the air.

In some embodiments of the present invention, a venting fixing frame is provided inside the cover to fix the bacteria-retaining breathable membrane. In some specific embodiments of the present invention, the venting fixing frame is a hollow gasket.

In some embodiments of the present invention, a sealing gasket is further provided inside the cover to enhance the sealing performance between the cover and the container body.

Figure 6:
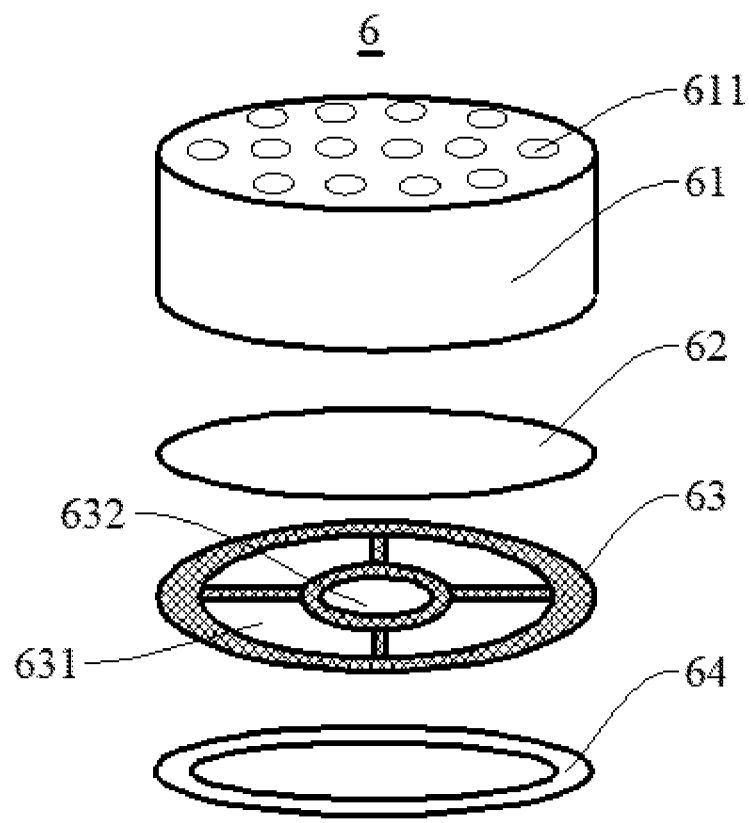
FIG. 6 is a schematic diagram of the exploded structure of the first cover of the present invention

FIG. 6 is a schematic diagram of an exploded structure of the first cover according to some embodiments of the present invention.

As shown in FIGS. 1, 5, and 6, the first cover 6 has a first outer cover 61, a bacteria-retaining breathable membrane 62, a hollow gasket 63 and a sealing gasket 64. The first outer cover 61 is a hollow cylinder with an lower end opening, and the upper end surface of the first outer cover 61 is provided with 9 air-permeable through holes 611 with the same structure. The bacteria-retaining breathable membrane 62 is fixed inside the first outer cover 61 through the hollow gasket 63. The hollow gasket 63 has a circular hollow hole 632 in the middle. The surface of the hollow gasket 63 is centered on the circular hollow hole 632. Four fan-shaped hollow holes 631 with the same structure are symmetrically disposed to facilitate air to enter the inside of the bioreactor 1 by passing through the first cover 6. The hollow gasket 63 is fixedly connected with the internal thread (not shown in the figure) of the inner sidewall of the first outer cover 61 by means of clamping. The external thread 1112 is utilized to detachably fixedly connect to the internal thread on the inner sidewall of the first outer cover 61 in a threaded coupled manner. The sealing gasket 64 is arranged to the lower end surface of the hollow gasket 63 to enhance the sealing performance between the first cover 6 and the cylindrical structure 111.

In some embodiments of the present invention shown in FIGS. 1, 5 and 6, after the first cover 6 is fixedly connected to the locking interface 1111 by threaded coupled, the upper end surface of the first cover 6 is not higher than the upper end surface of the cylindrical structure 111 to help protect the first cover 6 and facilitate the stacking of the bioreactor 1 during transportation.

In some embodiments of the present invention, during the transfer process of the bioreactor before use, the container body is sealed by a sealing cover. Remove the sealing cover before use and replace it with the cover.

In some embodiments of the present invention, the bacteria-retaining sealing breathable structure further has a barrier for sealing the open end of the container body so that the inside of the bioreactor is not contaminated before use.

In some embodiments of the present invention, a positioning adjusting member is provided inside the cover, the positioning adjusting member is provided between the bacteria-retaining breathable membrane and the barrier, and the rotation of the cover drives the positioning adjusting member moves toward the barrier to destroy the sealing performance of the barrier, so that the internal and external air pressures of the bioreactor are consistent during use.

In some embodiments of the present invention, the cover further has a spacing member, so that the lower end surface of the blade is located above the barrier.

In some embodiments of the present invention, the spacing member is a tear ring, and the barrier is a waterproof and breathable membrane.

Figure 7A:
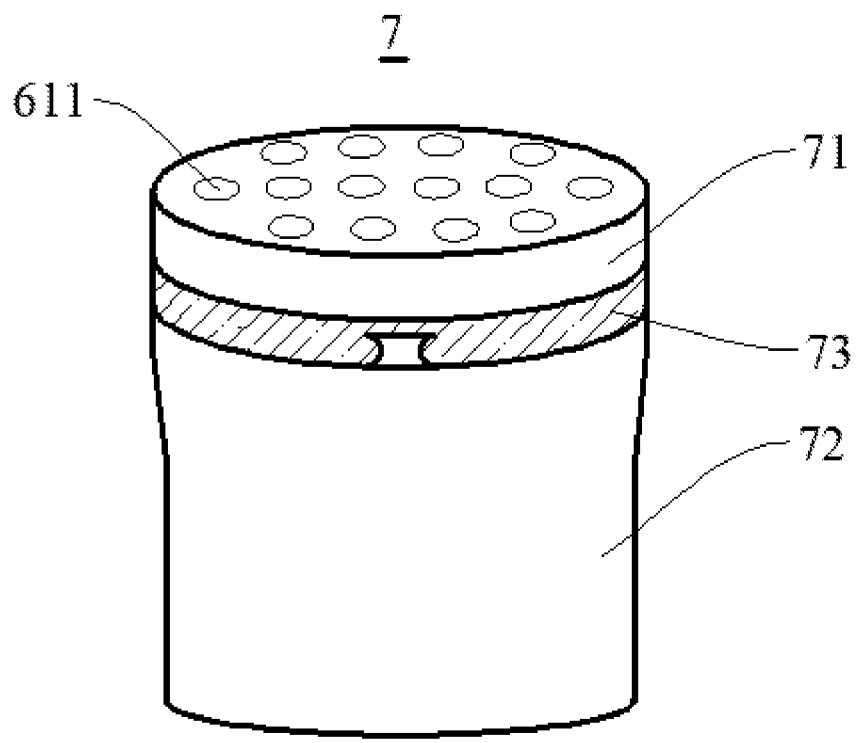
FIG. 7a is a schematic diagram of the structure of the second cover of the present invention.
Figure 7B:
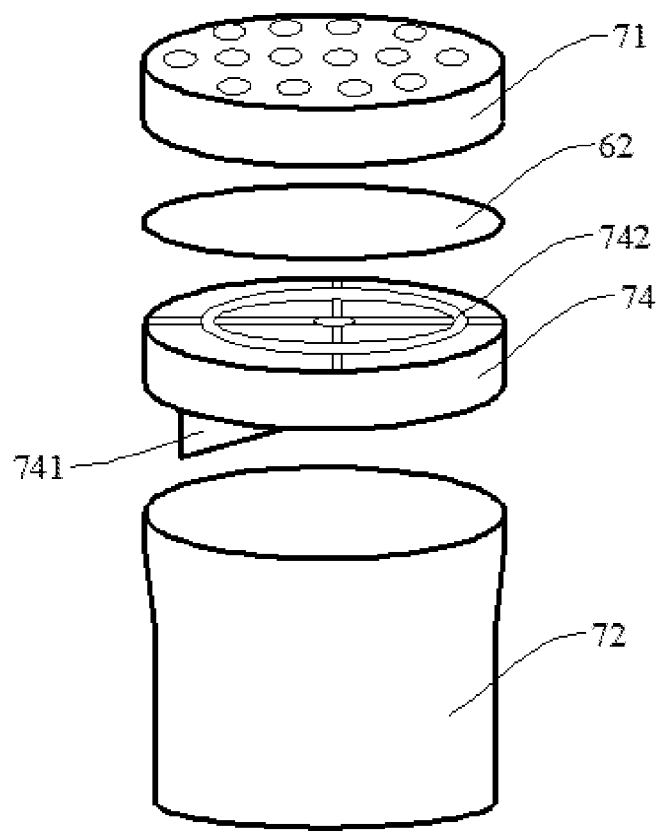
FIG. 7b is a schematic diagram of exploded structure of the second cover shown in FIG. 7a after the tear ring is removed.
Figure 7C:
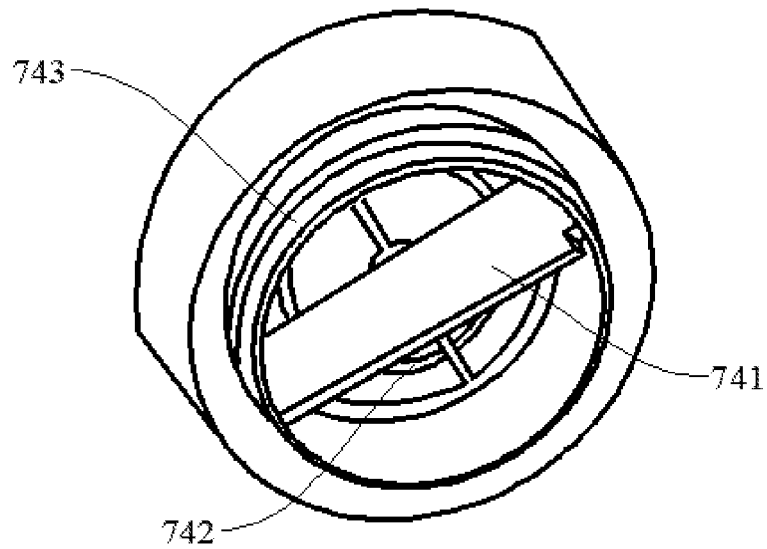

FIG. 7a is a schematic structural diagram of a second cover according to some embodiments of the present invention. FIG. 7b is a schematic diagram of the exploded structure of the second cover shown in FIG. 7a after the tear ring is removed. FIG. 7c is a schematic structural diagram of the positioning cover shown in FIG. 7a.

As shown in FIGS. 7a and 7b, the second cover 7 has an upper cover 71, a lower cover 72 and a tear ring 73. The inside of the second cover 7 is provided with the bacteria-retaining breathable membrane 62 and a positioning adjustment member (not shown in the figure). The positioning adjusting member (not shown in the figure) has a positioning cover 74 and a blade 741.

Specifically, referring to FIGS. 7a and 7b, the upper cover 71 is a hollow irregular cylinder with an open lower end, and the upper end surface has 14 air-permeable through holes 611. The antibacterial and bacteria-retaining breathable membrane 62 is fixed to the bottom of the upper cover 71 through the inner cover 74.

As shown in FIGS. 7b and 7c, the outer sidewall of the positioning cover 74 is fixedly connected to the inner sidewall of the upper cover 71. A fixing frame 742 is provided on the upper end surface of the positioning cover 74, and a rotating member 743 is provided inside. The upper end surface of the blade 741 is fixed to the lower end surface of the fixing frame 742. The side surface of the blade 741 is fixed on the inner sidewall of the rotating member 743, and part of the lower end surface is lower than the lower end surface of the positioning cover 74, in order to destroy the barrier (not shown in the figure) and fix the partially detached barrier (not shown in the figure) during the movement of the positioning cover 74 toward the barrier (not shown in the figure) and make sure that the internal and external air pressures of the bioreactor are consistent during use.

As shown in FIGS. 5, 7a to 7c, before removing the tear ring 73, the lower cover 72 is sleeved and fixed on the outside of the locking interface 1111, the lower cover 72 has an internal thread (not shown in the figure), a part of the internal thread (not shown in the figure) is fixedly connected with the external thread of the locking interface 1111 by threaded coupled, and the other part is screwed with the external thread of the outer sidewall of the rotating member 743, so that the lower end surface of the rotating member 743 reaches the first position 51, and the waterproof and breathable membrane (not shown in the figure) is located under the blade 741. By removing the tear ring 73, rotating the upper cover 71 clockwise, the rotating member 743 drives the blade 741 to move toward the waterproof and breathable membrane (not shown in the figure) to reach the second position 52 and cut the waterproof and breathable membrane (not shown in the figure), makes the internal and external air pressures of the bioreactor consistent.

The embodiment of the present invention also provides a biological reaction system, which has the bioreactor, a liquid supply unit, a liquid drain unit, a power drive unit, and a control unit.

Specifically, the liquid supply unit is fixedly connected to the liquid inlet portion and the cleaning liquid inlet portion, so as to deliver the replacement liquid to the liquid inlet portion and to deliver the cleaning liquid to the cleaning liquid inlet portion. The liquid drain unit is fixedly connected to the liquid outlet portion to discharge the replaced liquid or the cleaned liquid from the bioreactor; the power drive unit is used to drive the drive portion to move up and down; the control unit is used for rate control and time control of the lifting movement, and rate control and time control of the liquid supply unit and the drain unit.

Figure 8:
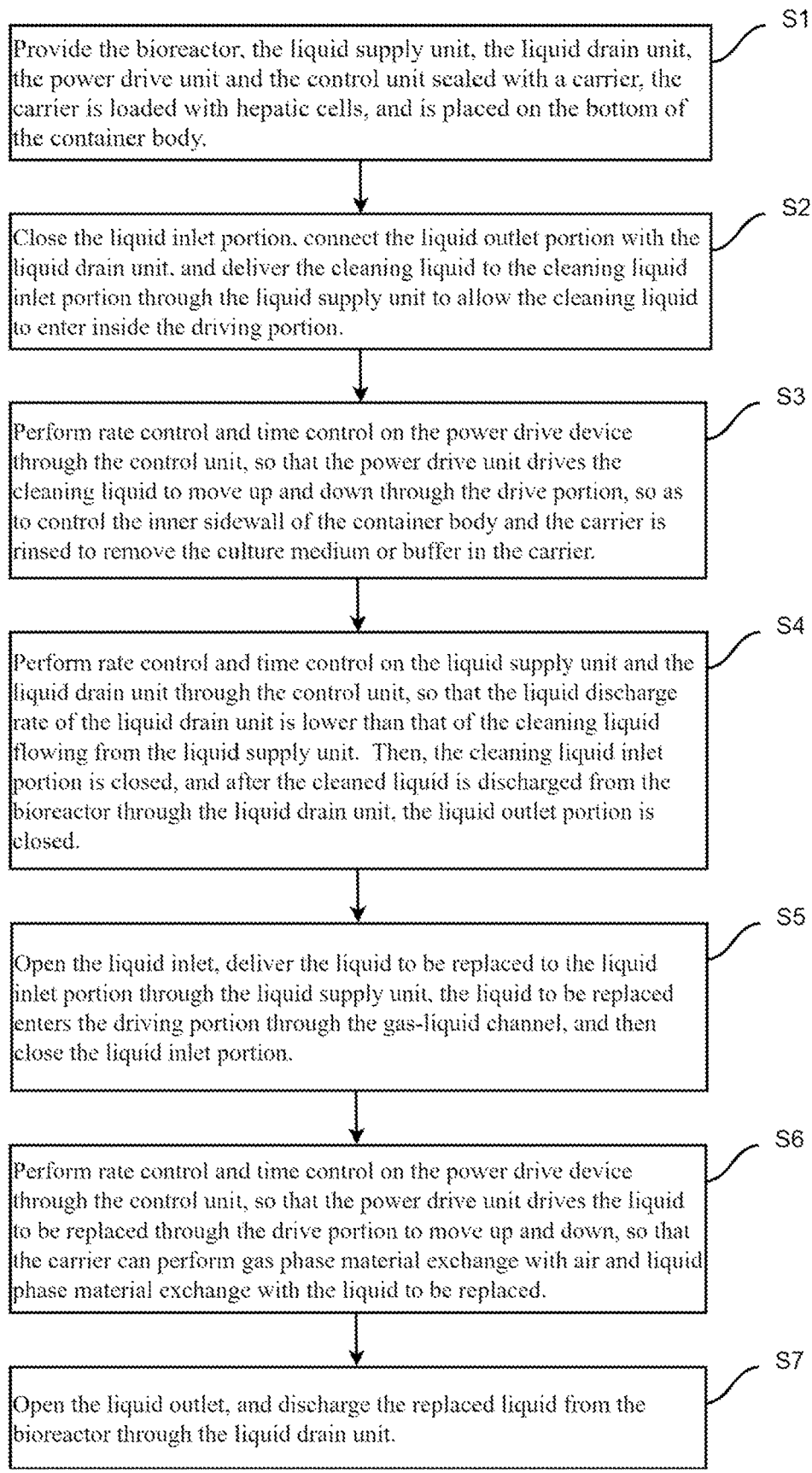
FIG. 8 is a flow chart of the operating method of the bioreactor of the present invention.

The embodiment of the present invention also provides an operating method of the bioreactor, referring to FIG. 8, comprising:

S1: Provide the bioreactor, the liquid supply unit, the liquid drain unit, the power drive unit and the control unit sealed with a carrier, the carrier is loaded with hepatic cells, and is placed on the bottom of the container body;

S2: Close the liquid inlet portion, connect the liquid outlet portion with the liquid drain unit, and deliver the cleaning liquid to the cleaning liquid inlet portion through the liquid supply unit to allow the cleaning liquid to enter inside the driving portion;

S3: Perform rate control and time control on the power drive device through the control unit, so that the power drive unit drives the cleaning liquid to move up and down through the drive portion, so as to control the inner sidewall of the container body and the carrier is rinsed to remove the culture medium or buffer liquid in the carrier;

S4: Perform rate control and time control on the liquid supply unit and the liquid drain unit through the control unit, so that the liquid discharge rate of the liquid drain unit is lower than that of the cleaning liquid flowing from the liquid supply unit. Then, the cleaning liquid inlet portion is closed, and after the cleaned liquid is discharged from the bioreactor through the liquid drain unit, the liquid outlet portion is closed;

S5: Open the liquid inlet, deliver the liquid to be replaced to the liquid inlet portion through the liquid supply unit, the liquid to be replaced enters the driving portion through the gas-liquid channel, and then close the liquid inlet portion;

S6: Perform rate control and time control on the power drive device through the control unit, so that the power drive unit drives the liquid to be replaced through the drive portion to move up and down, so that the carrier can perform gas phase material exchange with air and liquid phase material exchange with the liquid to be replaced;

S7: Open the liquid outlet, and discharge the replaced liquid from the bioreactor through the liquid drain unit.

In some embodiments of the present invention, the step S1 further includes: destroying the spacing member, and driving the positioning adjustment member to move toward the barrier through the rotation of the cover, so as to damage the sealing performance of the barrier the inside of the bioreactor, makes the internal and external air pressure of the bioreactor consistent.

In the step S3 of some specific embodiments of the present invention, the power driving device is a lifting platform, and the bioreactor is placed on the surface of the lifting platform, and is fixedly connected to the lifting platform through the threaded fasteners. The control unit is electrically connected to the lifting platform, and controls the movement speed of the lifting platform to be 5 mm/s, and the rinsing time to be 5 minutes. In the step S3 of some other specific embodiments of the present invention, the moving speed of the lifting platform is 0.5 mm/s, and the rinsing time is 10 minutes.

In step S4 of some specific embodiments of the present invention, the control unit controls the flow rate of the cleaning liquid from the liquid supply unit to be 0.5-5 mm/s.

In the step S5 of some specific embodiments of the present invention, the inflow rate of the liquid to be replaced controlled by the control unit is 0.5-5 mm/s.

In the step S6 of some embodiments of the present invention, the speed of the lifting movement is 0.5-5 mm/s, the time of the gas phase material exchange is 5-120 s in each lifting cycle, and the liquid phase material exchange time is 60-400 s. The gas phase material exchange time is the time when the carrier is above the liquid level of the replacement liquid, and the liquid phase material exchange time is the time when the carrier is below the liquid level of the replacement liquid.

Although the embodiments of the present invention are described in detail above, it is obvious to those skilled in the art that various modifications and changes can be made to these embodiments. However, it should be understood that such modifications and changes fall within the scope and spirit of the present invention described in the claims. Moreover, the present invention described here may have other embodiments, and may be implemented or realized in various ways.

What is claimed is:

1. A bioreactor applied to a bioartificial liver treatment system, comprising:
   a cover, a container body, a sealing portion, a driving portion and a liquid guide portion, the liquid guide portion having at least a liquid inlet portion, a cleaning liquid inlet portion, and a liquid outlet portion;
   wherein the cover is detachably and fixedly connected to the container body, and the cover is provided with a ventilation structure and a bacteria-retaining sealing breathable structure for making the internal and external air pressure of the bioreactor consistent;
   wherein the liquid inlet penetrates the sidewall of the container body to deliver the liquid to be replaced into the container body;
   wherein the cleaning liquid inlet portion includes a cleaning liquid inlet pipe that penetrates the bottom of the driving portion to communicate with the inside of the driving portion, so as to deliver cleaning liquid into the driving portion;

wherein the liquid outlet portion penetrates the sidewall and the bottom of the container body to discharge the replacement liquid or the cleaned liquid out of the bioreactor;

wherein a gas-liquid channel is opened at the bottom of the container body;

wherein the driving portion is used to drive the replacement liquid or the cleaning liquid to move up and down through elastic deformation; and wherein the sealing portion is arranged along the outer sidewall of the bioreactor, and is used for fixedly connecting the container body and the driving portion to prevent the liquid from flowing out of the sidewall of the bioreactor.

2. The bioreactor according to claim 1, wherein the gas-liquid channel is a plurality of arc-shaped hollow structures with the same structure, and the plurality of arc-shaped hollow structures surround the liquid outlet portion and are evenly distributed in a radial pattern with the junction of the bottom of the container body.

3. The bioreactor according to claim 1, wherein the driving portion is a bellow pipe structure with an open end.

4. The bioreactor according to claim 1, wherein the container body and the cover are detachably and fixedly connected by threaded coupled.

5. The bioreactor according to claim 1, wherein the ventilation structure is provided on the top of the cover, the bacteria-retaining sealing breathable structure includes a bacteria-retaining breathable membrane, and the bacteria-retaining breathable membrane is disposed on the lower end surface of the top of the cover has an average pore size of less than 0.22 microns to allow gas to pass freely, so that the internal and external air pressures of the bioreactor are consistent, and to block microorganisms in the air during use.

6. The bioreactor according to claim 1, wherein the bacteria-retaining sealing breathable structure further has a barrier to seal the open end of the container body, so that the inside of the bioreactor is not contaminated before using.

7. The bioreactor according to claim 6, further comprising a positioning adjustment member provided inside the cover, the positioning adjustment member is provided between the bacteria-retaining breathable membrane and the barrier, and the cover the rotating movement of the body drives the positioning adjustment member to move toward the barrier member to destroy the sealing performance of the barrier and make the internal and external air pressures of the bioreactor consistent during use.

8. The bioreactor according to claim 7, wherein the barrier is a waterproof and breathable membrane.

9. The bioreactor according to claim 7, wherein the positioning adjustment member has a positioning cover and a blade, and the blade is fixedly connected to the inner sidewall of the positioning cover, and the outer sidewall of the positioning cover is connected to the inner sidewall of the cover and is detachably fixedly connected, and at least part of the lower end surface of the blade is lower than the lower end surface of the positioning cover, so as to destroy and fix the barrier when the positioning cover moves toward the barrier, ensures that the internal and external air pressures of the bioreactor are consistent during use.

10. The bioreactor according to claim 9, wherein the cover further has a spacing member, so that the lower end surface of the blade is located above the barrier.

11. The bioreactor according to claim 10, wherein the spacing member is a tear ring, the tear ring divides the cover into an upper cover and a lower cover, and the upper cover passes through the positioning cover is fixedly connected with the lower cover, and the top of the upper cover is provided with an air-permeable structure.

12. The bioreactor according to claim 5, further comprising a venting fixing frame provided inside the cover, and the venting fixing frame detachably fixes the bacteria-retaining breathable membrane in the cover.

13. The bioreactor according to claim 12, further comprising a sealing gasket provided inside the cover, and the sealing gasket is provided on the lower end surface of the venting fixing frame to strengthen the cover body and the sealing performance between the container body.

14. The bioreactor according to claim 1, further comprising an elastic waterproof ring arranged between the inner sidewall of the sealing portion, the outer sidewall of the container body and the outer sidewall of the driving portion.

15. The bioreactor according to claim 1, further comprising at least one threaded fastener provided on the inner sidewall of the sealing portion to facilitate the fixation of the bioreactor.

16. A biological reaction system, comprising:
a liquid supply unit, a liquid drain unit, a power drive unit, a control unit, and the bioreactor according to claim 1;
wherein the liquid supply unit is fixedly connected to the liquid inlet portion and the cleaning liquid inlet pipe of the bioreactor, so as to deliver the replacement liquid to the liquid inlet portion and the cleaning liquid to the cleaning liquid inlet pipe;
wherein the liquid drain unit is fixedly connected to the liquid outlet portion of the bioreactor to discharge the replaced liquid or the cleaned liquid from the bioreactor;
wherein the power drive unit is used to drive the driving portion of the bioreactor to perform a lifting movement; and
wherein the control unit is used to perform rate control and time control on the lifting movement, and perform rate control and time control on the liquid supply unit and the liquid drain unit.

* * * * *